US012328809B2

United States Patent
Miyaoka et al.

(10) Patent No.: US 12,328,809 B2
(45) Date of Patent: Jun. 10, 2025

(54) CHARGED PARTICLE BEAM INJECTOR AND CHARGED PARTICLE BEAM INJECTION METHOD

(71) Applicants: KABUSHIKI KAISHA TOSHIBA, Tokyo (JP); TOSHIBA ENERGY SYSTEMS & SOLUTIONS CORPORATION, Kawasaki (JP)

(72) Inventors: Takeji Miyaoka, Chiba Chiba (JP); Daisuke Kameda, Asaka Saitama (JP)

(73) Assignees: Kabushiki Kaisha Toshiba, Tokyo (JP); Toshiba Energy Systems & Solutions Corporation, Kawasaki (JP)

( * ) Notice: Subject to any disclaimer, the term of this patent is extended or adjusted under 35 U.S.C. 154(b) by 214 days.

(21) Appl. No.: 18/168,233

(22) Filed: Feb. 13, 2023

(65) Prior Publication Data

US 2023/0199935 A1 Jun. 22, 2023

Related U.S. Application Data

(63) Continuation of application No. PCT/JP2021/029846, filed on Aug. 13, 2021.

(30) Foreign Application Priority Data

Oct. 13, 2020 (JP) .................. 2020-172727

(51) Int. Cl.
*H05H 7/08* (2006.01)
*A61N 5/10* (2006.01)
(Continued)

(52) U.S. Cl.
CPC ............. *H05H 7/08* (2013.01); *A61N 5/1078* (2013.01); *H05H 7/04* (2013.01); *H05H 9/00* (2013.01);
(Continued)

(58) Field of Classification Search
CPC ......... H05H 2277/11; H05H 2007/087; H05H 2007/082; H05H 9/00; H05H 7/08; H05H 7/04; G21K 5/04; A61N 2005/1087
See application file for complete search history.

(56) References Cited

U.S. PATENT DOCUMENTS 12,053,645 B2 * 8/2024 Liu ...................... A61N 5/1031
12,101,869 B2 * 9/2024 Mizushima ............ H05H 7/001
(Continued)

FOREIGN PATENT DOCUMENTS

CN 104548387 A 4/2015
EP 2400506 A1 * 12/2011 ............... A61B 6/00
(Continued)

OTHER PUBLICATIONS

Japan Patent Office, Int'l Search Report in Int'l Application No. PCT/JP2021/029846 (Sep. 14, 2021), 3 pages and translation, 2 pages.

*Primary Examiner* — Raymond R Chai
(74) *Attorney, Agent, or Firm* — Finnegan, Henderson, Farabow, Garrett & Dunner, LLP

(57) ABSTRACT

Provided is a technique by which each nuclide is optimized in terms of energy and number of particles and pre-accelerated so as to be injected into a main accelerator in charged particle beam irradiation by the combined use of different nuclides.

A charged particle beam injector includes: a first ion source that generates first nuclide ions; a first linear accelerator that linearly accelerates the generated first nuclide ions to form a first charged particle beam; a second ion source that generates second nuclide ions; a second linear accelerator that linearly accelerates the generated second nuclide ions to form a second charged particle beam; and a switching
(Continued)

electromagnet that injects one of the first charged particle beam and the second charged particle beam into an inflector of a main accelerator.

6 Claims, 3 Drawing Sheets

(51) Int. Cl.
 *H05H 7/04* (2006.01)
 *H05H 9/00* (2006.01)
 *H05H 13/04* (2006.01)
(52) U.S. Cl.
 CPC ............... *A61N 2005/1087* (2013.01); *H05H 2007/082* (2013.01); *H05H 2007/087* (2013.01); *H05H 13/04* (2013.01); *H05H 2277/11* (2013.01)

(56) References Cited

U.S. PATENT DOCUMENTS

| | | |
|---|---|---|
| 2004/0069958 A1 | 4/2004 | Dahl et al. |
| 2015/0115179 A1* | 4/2015 | Hiramoto ............. A61N 5/1048 250/492.3 |
| 2015/0133714 A1 | 5/2015 | Inaniwa et al. |
| 2020/0219695 A1* | 7/2020 | Hiasa .................... H01J 27/205 |
| 2022/0323790 A1* | 10/2022 | Arita .................... A61N 5/1079 |
| 2023/0209696 A1* | 6/2023 | Mizushima .......... A61N 5/1078 315/503 |

FOREIGN PATENT DOCUMENTS

| | | |
|---|---|---|
| JP | 2004-525486 A | 8/2004 |
| JP | 2013-233233 A | 11/2013 |
| JP | 2015-84886 A | 5/2015 |

* cited by examiner

CHARGED PARTICLE BEAM INJECTOR AND CHARGED PARTICLE BEAM INJECTION METHOD

CROSS-REFERENCE TO RELATED APPLICATIONS

This application is a Continuation Application of No. PCT/JP2021/029846, filed on Aug. 13, 2021, and the PCT application is based upon and claims the benefit of priority from Japanese Patent Application No. 2020-172727, filed on Oct. 13, 2020, the entire contents of which are incorporated herein by reference.

TECHNICAL FIELD

Embodiments of the present invention relate to a technique of pre-accelerating a charged particle beam and injecting it into (i.e., making it incident on) a main accelerator.

BACKGROUND

In particle beam therapy that is one of cancer treatment methods using radioactive rays, heavy particles such as carbon ions and protons, which are nuclei of hydrogen atoms, are accelerated by an accelerator to approximately 70% of the speed of light and then are intensively radiated onto a tumor. The particle beam therapy is painless in association with treatment and has fewer side effects than other radiotherapy, and thus, attention is focused on the particle beam therapy as a state-of-the-art treatment that can maintain quality of life (QoL) while achieving both treatment and social life.

For the purpose of improving the therapeutic effects of particle beam irradiation, it is considered to irradiate a tumor with charged particle beams in which different nuclides are used. Specifically, forms under consideration are: combined use of a proton beam and a heavy particle beam; and combined use of two or more types of heavy particle beams (carbon, helium, oxygen, neon, and the like).

PRIOR ART DOCUMENT

Patent Document

[Patent Document 1] JP 2015-084886 A

SUMMARY

Problems to be Solved by Invention

However, in the case of performing irradiation by the combined use of charged particle beams that are different in nuclide, there is a following problem. In the case of performing irradiation by the combined use of a carbon beam and a proton beam, number of particles required to obtain the same absorbed dose is more than one order of magnitude for protons than for carbons. For this reason, when pre-acceleration of the proton beam is performed by sharing a linear accelerator for the carbon beam, the number of proton particles to be contained in the charged particle beam becomes insufficient. In addition, when carbons and protons are injected into a circular accelerator (synchrotron) with the same energy by sharing the linear accelerator, the number of accumulated particles in the proton beam is reduced due to the space charge effect.

In view of the above-described circumstances, an object of embodiments of the present invention is to provide a technique by which each nuclide is optimized in terms of energy and number of particles and then is pre-accelerated so as to be injected into the main accelerator in charged particle beam irradiation by the combined use of different nuclides.

DETAILED DESCRIPTION

First Embodiment

Figure 1:
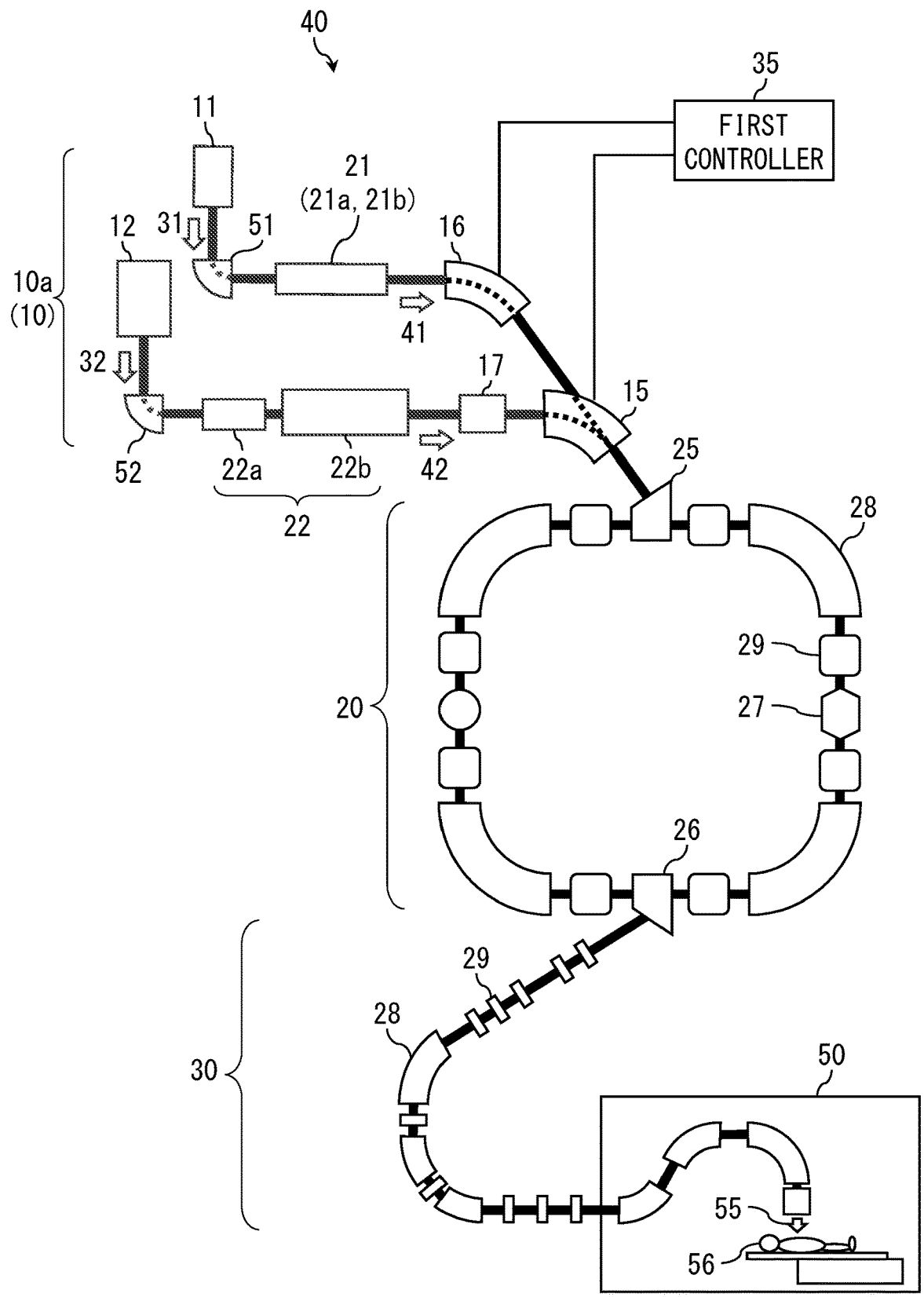
FIG. 1 is an overall configuration diagram of an accelerator system in which a charged particle beam injector according to the first embodiment of the present invention is adopted.

Hereinbelow, embodiments of the present invention will be described by referring to the accompanying drawings. FIG. 1 is an overall configuration diagram of an accelerator system 40 in which a charged particle beam injector 10a (10) according to the first embodiment of the present invention is adopted. The accelerator system 40 can be roughly divided into an injector 10, a main accelerator 20, and a beam transport system 30.

The injector 10a includes: a first ion source 11 that generates first nuclide ions 31; a first linear accelerator 21 that linearly accelerates the generated first nuclide ions 31 to form a first charged particle beam 41; a second ion source 12 that generates second nuclide ions 32; a second linear accelerator 22 that linearly accelerates the generated second nuclide ions 32 to form a second charged particle beam 42; and a switching electromagnet 15 that injects one of the first charged particle beam 41 and the second charged particle beam 42 into an inflector 25 of the main accelerator 20.

In the first embodiment, the first nuclide ions 31 are protons (hydrogen), and the second nuclide ions 32 are heavy particles (multivalent ions of a nuclide heavier than hydrogen), as exemplified by carbon, helium, oxygen, and neon. In the case of carbon ions $^{12}C^{6+}$ in the fully stripped state in which all the electrons are stripped off, the ratio of valence to mass number (hereinafter shortly referred to as a "valence/mass-number ratio") is 1/2. Each of the above-described helium ions $^{4}He^{2+}$, oxygen ions $^{16}O^{8+}$, and neon ions $^{20}Ne^{10+}$ has a valence/mass-number ratio of 1/2 in the fully stripped state, similarly.

Aspects of the first ion source 11 and the second ion source 12 include a laser-irradiation ion source in addition to a high-frequency (including microwave) irradiation ion source such as a PIG (Penning Ionization Gauge) ion source and an ECR (Electron Cyclotron Resonance) ion source. However, the ion sources are not limited to these, and any ion source that can efficiently generate the first nuclide ions 31 or the second nuclide ions 32 can be used as appropriate.

The ECR ion source utilizes the electron cyclotron resonance phenomenon to ionize neutral atoms into a plasma state. When raw material gas is introduced into the ECR ion source and microwaves are applied from the outside, ionized electrons are confined by a magnetic field, and these high-energy electrons collide with ions and/or atoms so as to eject electrons repeatedly, and thereby multivalent ions are generated.

In the first ion source 11 that generates protons, hydrogen gas is introduced as a raw material to generate hydrogen nuclei (protons) $^1H^+$. The proton $^1H^+$ has a mass-number of 1 and a valence Z of 1, and thus, its valence/mass-number ratio A is 1. When the hydrogen molecule ion $H_2^+$ is adopted as the proton beam, the mass number A is 2 and the valence number Z is 1, which gives the valence/mass-number ratio of 1/2. In the second ion source 12 that generates carbon heavy particles, methane gas ($CH_4$) to be used as the raw material is turned into plasma in a vacuum chamber to generate carbon ions $^{12}C^{4+}$. The carbon ion $^{12}C^{4+}$ has a mass number A of 12 and a valence Z of 4, and thus has a valence/mass-number ratio of 1/3.

As described above, the valence/mass-number ratio is 1/3 for carbon and is 1 for protons. Under the use of this fact, the first linear accelerator 21 configured to linearly accelerate the first charged particle beam (proton beam) can be made smaller in size than the second linear accelerator 22 configured to linearly accelerate the second charged particle beam (carbon beam). Since the first linear accelerator 21 and the second linear accelerator 22 are separately provided, the proton beam can be made larger in number of particles than the carbon beam and can have higher energy per nucleon than the carbon beam. This can equalize the absorbed doses per unit time between the carbon beam irradiation and the proton beam irradiation.

The linear accelerators 21 and 22 are composed of: RFQ (Radio Frequency Quadrupole) linear accelerators 21a and 22a; and drift tube linear accelerators (DTL: drift tube linacs) 21b and 22b, and accelerate nuclide ions 31 and 32 so as to output them as charged particle beams 41 and 42.

The RFQ linear accelerators 21a and 22a are connected to the downstream side of the ion sources 11 and 12, and each of the RFQ linear accelerators 21a and 22a has four electrodes (not shown) that form a quadrupole electric field by high frequency. The RFQ linear accelerators 21a and 22a simultaneously accelerate and converge the nuclide ions 31 and 32 from the ion sources 11 and 12 by the quadrupole electric fields.

The DTLs 21b and 22b includes: electrodes (not shown) that are connected to the respective output stages of the RFQ linear accelerators 21a and 22a and form electric fields along the central axis by high frequency; and drift tubes (not shown) that are disposed along the central axis so as to be spaced apart from each other. During the period in which the electric fields are in the traveling direction in parallel with the central axis, the DTLs 21b and 22b accelerate the charged particle beams 41 and 42. During the period in which the electric fields are in the direction opposite to the traveling direction, the DTLs 21b and 22b cause the charged particle beams 41 and 42 to pass through the drift tubes, and thereby stepwise accelerate the charged particle beams 41 and 42. In this manner, the linear accelerators 21 and 22 accelerate the nuclide ions 31 and 32 injected from the ion sources 11 and 12 so as to form the charged particle beams 41 and 42 having predetermined energies, and then emit the charged particle beams 41 and 42.

The switching electromagnet 15 having been set to a non-excitation mode causes the first charged particle beam 41 to travel straight and injects the first charged particle beam 41 into the inflector 25 of the main accelerator 20. The switching electromagnet 15 having been set to an excitation mode bends the second charged particle beam 42 by electromagnetic force so as to inject the second charged particle beam 42 into the inflector 25. This inflector 25 can be applied without changing its specifications when the energy of the first charged particle beam 41 of protons is about twice the energy of the second charged particle beam 42 of carbon.

The nuclide ions 31 and 32 to be generated from the ion sources 11 and 12 have different energies and are mixed with unintended impurity ions. Thus, it is necessary to extract only the nuclide ions 31 and 32 having the specified energies in accordance with the specifications and inject the extracted nuclide ions 31 and 32 into the linear accelerators 21 and 22.

For this reason, the injector 10a further includes: a first extraction electromagnet 51 that bends the generated first nuclide ions 31 by electromagnetic force and then injects the first nuclide ions 31 into the first linear accelerator 21; and a second extraction electromagnet 52 that bends the generated second nuclide ions 32 by electromagnetic force and then injects the second nuclide ions 32 into the second linear accelerator 22. Causing the nuclide ions 31 and 32 to pass through the extraction electromagnets 51 and 52 energized to respective predetermined setting values can eliminate unintended ions that are different from the nuclide ions 31 and 32 having predetermined energies.

The injector 10a further includes a bending electromagnet 16 that bends the first charged particle beam 41 emitted from the first linear accelerator 21 by electromagnetic force and then injects the first charged particle beam 41 into the inflector 25 of the main accelerator 20. This configuration can eliminate unintended ions contained in the first charged particle beam 41.

Moreover, in the injector 10a, the emission side of the second linear accelerator 22 is provided with a stripper 17 that strips the core electrons of the nuclide ions of the second charged particle beam 42. Although illustration is omitted, the stripper 17 may also be disposed on the emission side of the first linear accelerator 21 in some cases.

Although the carbon ions $^{12}C^{4+}$ to be generated by the second ion source 12 are ions from which only the peripheral electrons have been separated, the carbon ions $^{12}C^{4+}$ have their core electrons separated by passing through the stripper 17. As a result, the carbon ions $^{12}C^{4+}$ are converted into fully striped carbon ions $^{12}C^{6+}$ in which all the electrons are stripped off, and its valence/mass-number ratio changes from 1/3 to 1/2, which improves the acceleration of the second charged particle beam 42.

A first controller 35 sets only one of the switching electromagnet 15 and the bending electromagnet 16 to the excitation mode, and sets the other of the switching electromagnet 15 and the bending electromagnet 16 to the non-excitation mode. Under such setting, only the charged particle beam having an arcuate trajectory due to setting of the excitation mode is injected into the inflector 25 of the main accelerator 20.

When the switching electromagnet 15 is set to the non-excitation mode and the bending electromagnet 16 is set to the excitation mode, the second charged particle beam 42 does not enter the inflector 25, and only the first charged particle beam 41 enters the inflector 25. Conversely, when the switching electromagnet 15 is set to the excitation mode and the bending electromagnet 16 is set to the non-excitation mode, the first charged particle beam 41 does not enter the inflector 25, and only the second charged particle beam 42 enters the inflector 25. Further, the switching electromagnet 15 having been set to the excitation mode has a function of eliminating unintended ions contained in the second charged particle beam 42.

Although a description has been given of the case where the first nuclide ions 31 are protons and the second nuclide ions 32 are heavy particles in the present embodiment, the respective nuclides of the first and second nuclide ions 31 and 32 are exchanged in some cases, and are both heavy particles different from each other in some cases.

Although a circular accelerator such as a synchrotron is used for the main accelerator 20, the main accelerator 20 is not particularly limited to such a case. This synchrotron 20 includes: a high-frequency acceleration cavity 27 configured to accelerate the charged particle beams 41 and 42 injected from the injector 10 by high-frequency power; a plurality of bending electromagnets 28 configured to generate a magnetic field that bends the orbiting charged particles; a plurality of quadrupole electromagnets 29 configured to generate a magnetic field that diverges and converges the orbiting charged particles and keeps them in the orbit; and a deflector 26 configured to emit the charged particles orbiting around the synchrotron 20 into the beam transport system 30.

On the basis of the above-described configuration, the low-energy first charged particle beam 41 or second charged particle beam 42 emitted from the injector 10 is injected into the inflector 25, then orbits the synchrotron 20, then is accelerated to 70% to 80% of the speed of light, and then is caused to change its traveling direction from the orbit by the deflector 26 so as to be extracted into the beam transport system 30 when reaching a predetermined high energy.

The beam transport system 30 is also provided with: the quadrupole electromagnet 29 for keeping the charged particles traveling straight within the trajectory; and the bending electromagnet 28 for bending the trajectory of the charged particles. To the output side of this beam transport system 30, an irradiator 50 configured to treat a tumor of a patient 56 by irradiating the tumor with a charged particle beam 55 is connected. This irradiator 50 is only one aspect, and the facility to be connected to the output side of the beam transport system 30 is not particularly limited.

Second Embodiment

Figure 2:
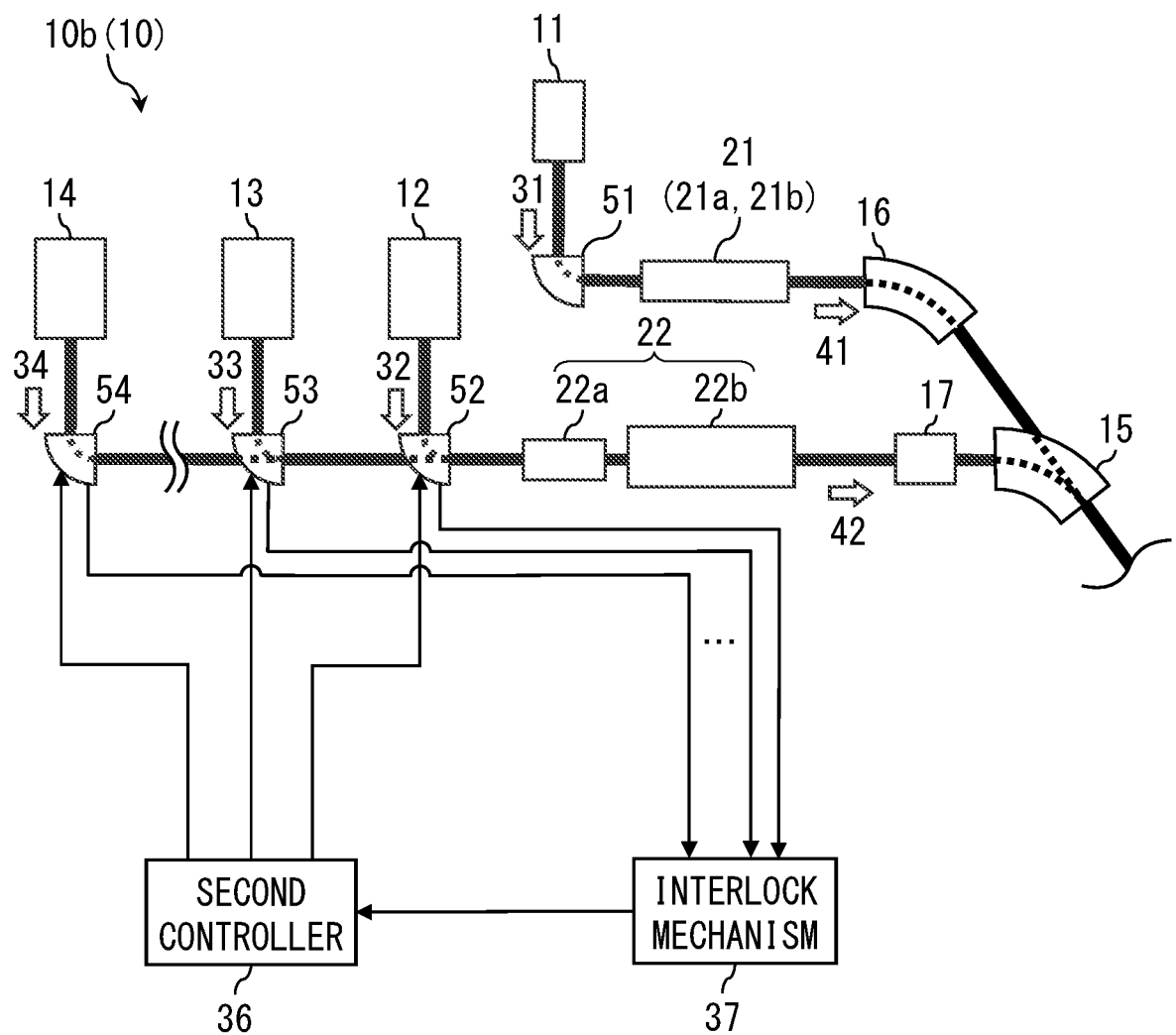
FIG. 2 is a configuration diagram illustrating a charged particle beam injector according to the second embodiment.

Next, the second embodiment of the present invention will be described by referring to FIG. 2. FIG. 2 is a configuration diagram illustrating a charged particle beam injector 10b (10) according to the second embodiment. In FIG. 2, each component having the same configuration or function as those in FIG. 1 is denoted by the same reference sign, and duplicate description is omitted.

In addition to the configuration of the first embodiment (i.e., the first ion source 11, the first linear accelerator 21, the second ion source 12, the second linear accelerator 22, and the switching electromagnet 15), the injector 10b according to the second embodiment further includes: a third ion source 13 that generates third nuclide ions 33; and a third extraction electromagnet 53 that bends the generated third nuclide ions 33 by electromagnetic force and then causes the third nuclide ions 33 to pass straight through the second extraction electromagnet 52 and enter the second linear accelerator 22.

The injector 10b further includes a fourth extraction electromagnet 54. The fourth extraction electromagnet 54 bends generated fourth nuclide ions 34 by electromagnetic force, and causes the fourth nuclide ions 34 to pass straight through the third extraction electromagnet 53 and the second extraction electromagnet 52 and enter the second linear accelerator 22. In this manner, number of ion sources can be increased in the second embodiment.

A second controller 36 sets only one of the plurality of extraction electromagnets 52, 53, and 54 to the excitation mode, and sets the rest of the extraction electromagnets 52, 53, and 54 to the non-excitation mode. Under such setting, the nuclide ions only from the ion sources having been set to the excitation mode and connected to the extraction electromagnet can be sent into the acceleration trajectory.

The injector 10b further includes an interlock mechanism 37 that outputs an interlock signal on the basis of the respective excitation states of the plurality of extraction electromagnets 52, 53, and 54 arranged on the same particle-beam trajectory. The magnetic fields to be formed by the respective extraction electromagnets 52, 53, and 54 are set to magnetic flux densities suitable for the nuclide ions 32, 33, and 34 to pass through their trajectories.

The interlock mechanism 37 acquires the magnetic flux density measured in each of the extraction electromagnets 52, 53, and 54. When the acquired magnetic flux density is out of the range having been preset for the nuclide ions to be injected, the interlock mechanism 37 outputs the interlock signal so as to stop supply of the charged particle beam to the main accelerator 20.

There is a demand for continuous irradiation of charged particle beams by switching different nuclide ions in a short time. In the second embodiment, the plurality of extraction electromagnets 52, 53, and 54 are arranged on the linear trajectory of the charged particle beam 42, and are respectively connected to the ion sources 12, 13, and 14. Since such a configuration is adopted, a plurality of heavy particle ions can be switched and continuously radiated as a charged particle beam with one set of linear accelerator.

Regarding carbon, helium, oxygen, and neon exemplified as heavy particles, their valence/mass-number ratio in the fully stripped state immediately before entering the main accelerator 20 is 1/2, as described above. In the case of these nuclides in the fully stripped state, they all have the same valence/mass-number ratio and it is difficult to detect the contamination of unintended ions in the charged particle beam.

Immediately after being generated from the ion source 11, 12, 13, or 14, the valence/mass-number ratio is 1/3 for carbon ions $^{12}C^{4+}$, 1/2 for helium ions $^{4}He^{2+}$, and 5/16 for oxygen ion $^{16}O^{5+}$, and the charged particle beam is not contaminated with unintended ions as long as the respective excitation modes of the extraction electromagnets 52, 53, and 54 are ideally set.

Thus, when the magnetic flux density measured by the extraction electromagnet 52, 53, or 54 is out of the predetermined range, the interlock signal is outputted to indicate a possibility that unintended ions are mixed in the charged particle beam. This is because irradiating a patient with a nuclide different from the treatment plan is an event that must be absolutely avoided in terms of nature of treatment.

Figure 3:
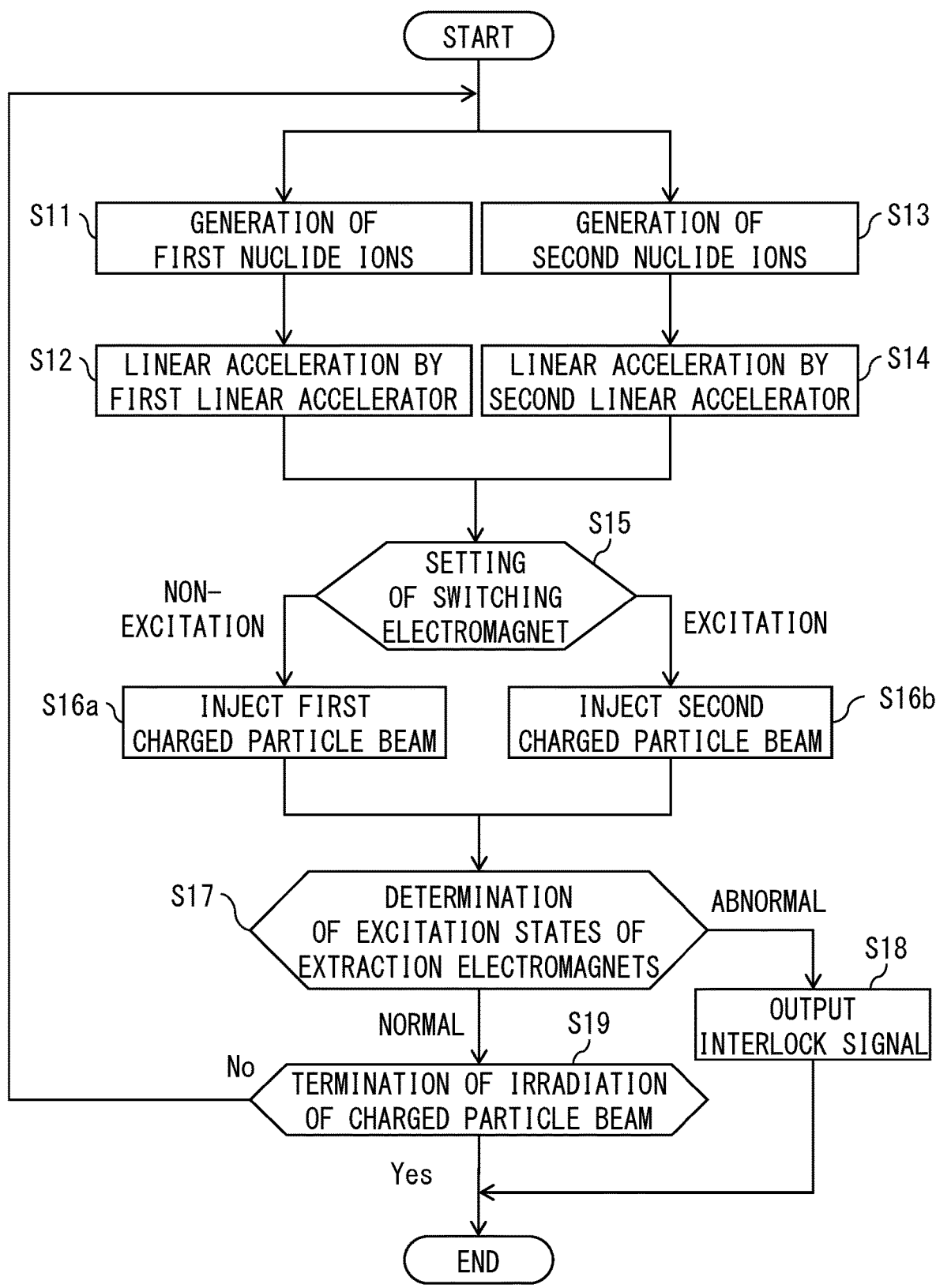
FIG. 3 is a flowchart illustrating a charged particle beam injection method according to the embodiment.

A charged particle beam injection method according to the present embodiment will be described on the basis of the flowchart of FIG. 3 by referring to FIG. 1 and FIG. 2 as required.

First, in the step S11, the first nuclide ions 31 are generated in the first ion source 11.

In the step S12, the generated first nuclide ions 31 are linearly accelerated by the first linear accelerator 21 to form the first charged particle beam 41.

In the step S13, the second nuclide ions 32 are generated in the second ion source 12.

In the step S14, the generated second nuclide ions 32 are linearly accelerated by the second linear accelerator 22 to form the second charged particle beam 42.

In the step S15, the switching electromagnet 15 is set in such a manner that one of the first charged particle beam 41 and the second charged particle beam 42 is injected into the inflector 25 of the main accelerator 20. At this time, if the switching electromagnet 15 is set to the non-excitation mode, in the step S16a, the first charged particle beam 41 is injected. If the switching electromagnet 15 is set to the excitation mode, in the step S16b, the second charged particle beam 42 is injected.

In all of the steps S11 to S16 described above, the interlock mechanism 37 determines the excitation state of each of the extraction electromagnets 52, 53 and 54 (in the step S17). If the excitation state is determined to be abnormal, the interlock signal is immediately outputted to stop the injection of the charged particle beam (END).

While the excitation state in each of the extraction electromagnets 52, 53, and 54 continues to be determined as normal, the charged particle beams 41 and 42 pass through the beam transport system 30, and the processing of the steps S11 to S17 is continuously performed until the irradiation in the irradiator 50 is completed (S19, No, Yes, END).

According to at least one embodiment of the charged particle beam injector described above, in the case of using a combination of different nuclides for irradiation of a charged particle beam, each nuclide is optimized in terms of energy and number of particles and then is pre-accelerated so as to be injected into the main accelerator by using 2 separate linear accelerators.

While certain embodiments have been described, these embodiments have been presented by way of example only, and are not intended to limit the scope of the inventions. These embodiments may be embodied in a variety of other forms, and various omissions, substitutions, and changes may be made without departing from the spirit of the inventions. These embodiments and their modifications are included in the accompanying claims and their equivalents as well as included in the scope and gist of the inventions.

The invention claimed is:

1. A charged particle beam injector comprising:
a first ion source that generates first nuclide ions;
a first linear accelerator that linearly accelerates the first nuclide ions to form a first charged particle beam;
a second ion source that generates second nuclide ions;
a second linear accelerator that linearly accelerates the second nuclide ions to form a second charged particle beam;
a switching electromagnet that injects one of the first charged particle beam and the second charged particle beam into an inflector of a main accelerator;
a first extraction electromagnet that bends the first nuclide ions by electromagnetic force and injects the first nuclide ions into the first linear accelerator;
a second extraction electromagnet that bends the second nuclide ions by electromagnetic force and injects the second nuclide ions into the second linear accelerator;
a third ion source that generates third nuclide ions; and
a third extraction electromagnet that bends the third nuclide ions by electromagnetic force, then causes the third nuclide ions to pass straight through the first extraction electromagnet or the second extraction electromagnet, and then injects the third nuclide ions into the first linear accelerator or the second linear accelerator.

2. The charged particle beam injector according to claim 1, wherein an interlock signal is outputted based on excitation states of a plurality of extraction electromagnets disposed on a same particle beam trajectory.

3. The charged particle beam injector according to claim 1, further comprising a bending electromagnet that bends the first charged particle beam emitted from the first linear accelerator by electromagnetic force and injects the first charged particle beam into the inflector,
wherein the switching electromagnet is configured to bend the second charged particle beam emitted from the second linear accelerator by electromagnetic force and inject the second charged particle beam into the inflector.

4. The charged particle beam injector according to claim 1, wherein a stripper configured to strip core electrons from nuclide ions is provided at an emission side of at least one of the first linear accelerator and the second linear accelerator.

5. The charged particle beam injector according to claim 1, wherein one of the first nuclide ions and the second nuclide ions are hydrogen ions, and other of the first nuclide ions and the second nuclide ions are multivalent ions of a nuclide heavier than hydrogen.

6. A charged particle beam injection method comprising steps of:
generating first nuclide ions in a first ion source;
linearly accelerating the first nuclide ions by using a first linear accelerator to form a first charged particle beam;
generating second nuclide ions in a second ion source;
linearly accelerating the second nuclide ions by using a second linear accelerator to form a second charged particle beam;
injecting one of the first charged particle beam and the second charged particle beam into an inflector of a main accelerator by setting of a switching electromagnet,
wherein the method further comprising:
bending the first nuclide ions by electromagnetic force and injecting the first nuclide ions into the first linear accelerator by using a first extraction electromagnet;
bending the second nuclide ions by electromagnetic force and injecting the second nuclide ions into the second linear accelerator by using a second extraction electromagnet;
generating third nuclide ions in a third ion source; and
bending the third nuclide ions by electromagnetic force, then causing the third nuclide ions to pass straight through the first extraction electromagnet or the second extraction electromagnet, and then injecting the third nuclide ions into the first linear accelerator or the second linear accelerator, by using a third extraction electromagnet.

* * * * *